US011806256B2

(12) United States Patent
Harmon et al.

(10) Patent No.: US 11,806,256 B2
(45) Date of Patent: Nov. 7, 2023

(54) THREE DIMENSIONAL PRINT METHOD AND PART

(71) Applicant: TriFusion Devices Inc., Pflugerville, TX (US)

(72) Inventors: Garrett Harmon, Pflugerville, TX (US); Shannon Hazel, Bryan, TX (US); Charles Brandon Sweeney, Pflugerville, TX (US); Blake Teipel, Pflugerville, TX (US)

(73) Assignee: ESSENTIUM IPCO, LLC, Pflugerville, TX (US)

( * ) Notice: Subject to any disclaimer, the term of this patent is extended or adjusted under 35 U.S.C. 154(b) by 435 days.

(21) Appl. No.: 16/758,716

(22) PCT Filed: Oct. 23, 2018

(86) PCT No.: PCT/US2018/057084

§ 371 (c)(1),
(2) Date: Apr. 23, 2020

(87) PCT Pub. No.: WO2019/083988

PCT Pub. Date: May 2, 2019

(65) Prior Publication Data

US 2020/0337871 A1 Oct. 29, 2020

Related U.S. Application Data

(60) Provisional application No. 62/575,810, filed on Oct. 23, 2017.

(51) Int. Cl.
*A61F 2/80* (2006.01)
*B33Y 10/00* (2015.01)
(Continued)

(52) U.S. Cl.
CPC .............. *A61F 2/80* (2013.01); *A61F 2/5046* (2013.01); *B33Y 10/00* (2014.12); *B33Y 80/00* (2014.12); *A61F 2240/002* (2013.01)

(58) Field of Classification Search
None
See application file for complete search history.

(56) References Cited

U.S. PATENT DOCUMENTS 1,032,074 A * 7/1912 Marks ........................ A61F 2/60 623/32
2,253,040 A * 8/1941 Martino .................... A61F 2/80 623/36

(Continued)

FOREIGN PATENT DOCUMENTS

EP 2196173 A2 6/2010
WO WO-9321865 A1 * 11/1993 ............... A61F 2/60

(Continued)

OTHER PUBLICATIONS

Extended European Search Report in 18870769.9, European Patent Office (EPO), dated Nov. 8, 2021.

(Continued)

*Primary Examiner* — Brian A Dukert
*Assistant Examiner* — Melissa A Hoban
(74) *Attorney, Agent, or Firm* — Vivacqua Crane, PLLC

(57) ABSTRACT

A prosthetic socket for a prosthetic limb is provided. The prosthetic socket comprises a socket body and a first and second structural members. The socket body comprises a distal end and a top edge opposite the distal end. The distal end comprises a prosthetic component attachment mechanism. The top edge comprises a medial fin, a lateral fin, a posterior edge and an anterior edge. The first and second structural members each include a first straight portion, a second straight portion, and a first arch portion. The first structural member is disposed on a medial exterior surface (Continued)

36
12
R
10
18
16
24
34
34
20
22 of the socket body and the second structural member is disposed on an lateral exterior surface of the socket body.

17 Claims, 3 Drawing Sheets

(51) Int. Cl.
*B33Y 80/00* (2015.01)
*A61F 2/50* (2006.01)

(56) References Cited

U.S. PATENT DOCUMENTS 3,309,714 A * 3/1967 Porten .................. A61F 2/7843 623/37
3,548,420 A * 12/1970 Spence ................. A61F 2/7812 128/892
4,128,903 A * 12/1978 Marsh ...................... A61F 2/80 623/36
5,246,464 A * 9/1993 Sabolich .................. A61F 2/80 623/33
5,405,405 A * 4/1995 Love ..................... A61F 2/7843 264/222
6,077,300 A 6/2000 Sabolich et al.
10,179,056 B2 * 1/2019 Hurley ...................... A61F 2/80
2006/0179935 A1 * 8/2006 Warila ...................... A61F 2/76 73/172
2007/0123998 A1 * 5/2007 Egilsson ............... A61F 2/7812 623/36
2009/0076426 A1 * 3/2009 Einarsson ............ A61F 5/0123 602/26
2010/0161076 A1 6/2010 Pallari
2010/0274364 A1 * 10/2010 Pacanowsky ............ A61F 2/80 600/595
2012/0303135 A1 * 11/2012 Vo ............................ A61F 2/60 623/53
2013/0053981 A1 2/2013 Alley et al.
2014/0249650 A1 * 9/2014 Laghi .................... D04B 35/36 28/142
2015/0265432 A1 * 9/2015 King .................... A61F 2/7812 623/34
2015/0328840 A1 11/2015 Zachariasen et al.
2015/0352793 A1 12/2015 Zukoski et al.
2016/0143752 A1 5/2016 Hurley et al.
2016/0184113 A1 6/2016 Koniuk
2016/0331562 A1 * 11/2016 Bache ...................... A61F 2/80
2017/0105853 A1 * 4/2017 Jonsson ................... A61F 2/80
2017/0129195 A1 * 5/2017 Stephenson ........... B33Y 10/00
2017/0143520 A1 5/2017 Hurley et al.
2017/0246013 A1 8/2017 Erenstone
2019/0374355 A1 * 12/2019 Størup ................. A61F 2/7812

FOREIGN PATENT DOCUMENTS

WO 2012167384 A1 12/2012
WO 2015013560 A1 1/2015

OTHER PUBLICATIONS

International Search Report and Written Opinion in PCT/US18/57084, United States Patent & Trademark Office as International Searching Authority, dated Jan. 17, 2019.
Search report in 201880078307.X, China National Intellectual Property Administration, dated Mar. 2, 2022, 7 pages.

* cited by examiner

THREE DIMENSIONAL PRINT METHOD AND PART

CROSS REFERENCE TO RELATED APPLICATION

This application is the National Stage of International Application No. PCT/US2018/057084, filed Oct. 23, 2018 and claims the benefit U.S. Provisional Patent Application Ser. No. 62/575,810, filed Oct. 23, 2017, the disclosures of which are hereby incorporated in its entirety herein by reference.

FIELD

The invention relates to manufacturing methods for three dimensional parts and in particular to three dimensional printing methods and parts produced by the manufacturing method.

BACKGROUND

The statements in this section merely provide background information related to the present disclosure and may or may not constitute prior art.

Prosthetic limbs typically include a residual limb socket and a distal prosthetic component. The prosthetic socket is the portion of the prosthesis designed to fit on the residual limb, retain the residual limb securely, and mount the distal prosthetic component. If the prosthetic socket does not fit to the residual limb properly, the patients comfort will inevitably be compromised thus resulting in an unusable prosthetic.

Recent improvements in the manufacture of prosthetic sockets have greatly enhanced the comfort and fit of the socket to the residual limb. However, most of the improvements have come at a high cost by using expensive materials and time consuming manufacturing techniques. For example, many high quality prosthetics include carbon fiber for greatly improved strength. A carbon fiber socket uses manufacturing techniques that includes taking a cast of the residual limb, making a mold from the casting, and combining the carbon fiber and resin around the mold. This technique is not only time consuming but it is also very expensive as the result of the materials used to provide strength and rigidity. The cost and complexity of this manufacturing process easily puts such a high quality prosthetic out of reach for many of those patients that may benefit from such an improved prosthetic.

Even more recently, three dimensional printing or additive printing technology has evolved into providing very accurate printed parts in a quick and efficient manner at a low cost. A three dimensional print of a prosthetic socket starts with only a dimensional scan of the residual limb and a conversion to a CAD model of the socket. A “hard copy” of the CAD model is reproduced by the three dimensional printing device and fit with the distal prosthetic component for a near perfect fit to the residual limb. However, while the comfortable fit is one requirement for the socket, high strength is another. The current state of three dimensional printing of lightweight thermoplastic parts does not provide the high strength required by prosthetic sockets in heavy or medium duty applications. Furthermore, if a high strength socket is provided, the socket design required thicker materials and is much heavier and less comfortable for the patient. Thus there is a trade-off between strength and weight. Eventually, even in light duty application, three dimensional printed prosthetic sockets fail at much quicker in service. Therefore, the technique fails to provide as large of a benefit as possible.

While current viable prosthetic manufacturing techniques provide high quality prosthetic limbs, there is a need for a method that provides a prosthetic socket having improved strength, comfort, cost, and timing.

SUMMARY

The present disclosure provides a prosthetic socket for a prosthetic limb, the prosthetic socket comprising a socket body and a first structural member. The socket body comprises a distal end and a top edge opposite the distal end. The distal end comprises a prosthetic component attachment mechanism. The first structural member comprises a first straight portion, a second straight portion, and a first arch portion. The first structural member is disposed on an exterior surface of the socket body.

In one example of the present disclosure, the first straight portion of the first structural member comprises a first end fixed to a second end of the second straight portion of the first structural member. A third end of the first arch portion is fixed to a fourth end of the first straight portion. A fifth end of the first arch portion is fixed to a sixth end of the second straight portion of the first structural member.

In another example of the present disclosure, the socket body further comprises a medial fin disposed on the top edge of the socket body. The first arch member of the first structural member is disposed on the medial fin of the top edge of the socket body.

In yet another example of the present disclosure, the socket body further comprises a second structural member having a third straight portion, a fourth straight portion, and a second arch portion. The second structural member is disposed on a lateral exterior surface of the socket body.

In yet another example of the present disclosure, the third straight portion of the second structural member comprises a seventh end fixed to an eighth end of the fourth straight portion of the second structural member. A ninth end of the second arch portion is fixed to a tenth end of the third straight portion. An eleventh end of the first arch portion is fixed to a twelfth end of the fourth straight portion of the second structural member.

In yet another example of the present disclosure, the socket body further comprises a lateral fin disposed on the top edge of the socket body. The second arch member of the second structural member is disposed on the lateral fin of the top edge of the socket body.

In yet another example of the present disclosure, a first cross section of the socket body includes a first wall thickness from about 0.1 mm to about 20 mm.

In yet another example of the present disclosure, a second cross section of the first structural member includes a second wall thickness from about 0.25 mm to about 100 mm.

In yet another example of the present disclosure, the socket body further comprises a posterior edge and an anterior edge, the posterior edge is disposed on the top edge connecting the medial fin with the lateral fin, the anterior edge is disposed on the top edge opposite the posterior edge connecting the medial fin to the lateral fin, and the posterior edge and anterior edge have a scalloped shape.

In yet another example of the present disclosure, the socket body further comprises an interior surface having a negative shape of a residual limb of a wearer.

The present disclosure also provides a method of manufacturing a prosthetic socket for a wearer. The method includes a first step of creating a CAD model of surface data of a surface of a residual limb of the wearer. A second step includes converting the CAD model of surface data into a CAD model of volume data of the socket body by adding wall thickness to the CAD model of surface data. A third step includes adding a CAD model of volume data of a medial structural member and a lateral structural member to the CAD model of volume data of the socket body resulting in a CAD model of volume data of the prosthetic socket. A fourth step includes converting the CAD model of volume data of the prosthetic socket to a three dimensional print path file. A fifth step includes printing the three dimensional print path file using a three dimensional printer.

In one example of the present disclosure, another step of the method includes adding a CAD model of volume data of a distal end to the CAD model of volume data of the prosthetic socket.

Other examples and advantages of the invention will be explained in further detail by reference to the following description and appended drawings.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
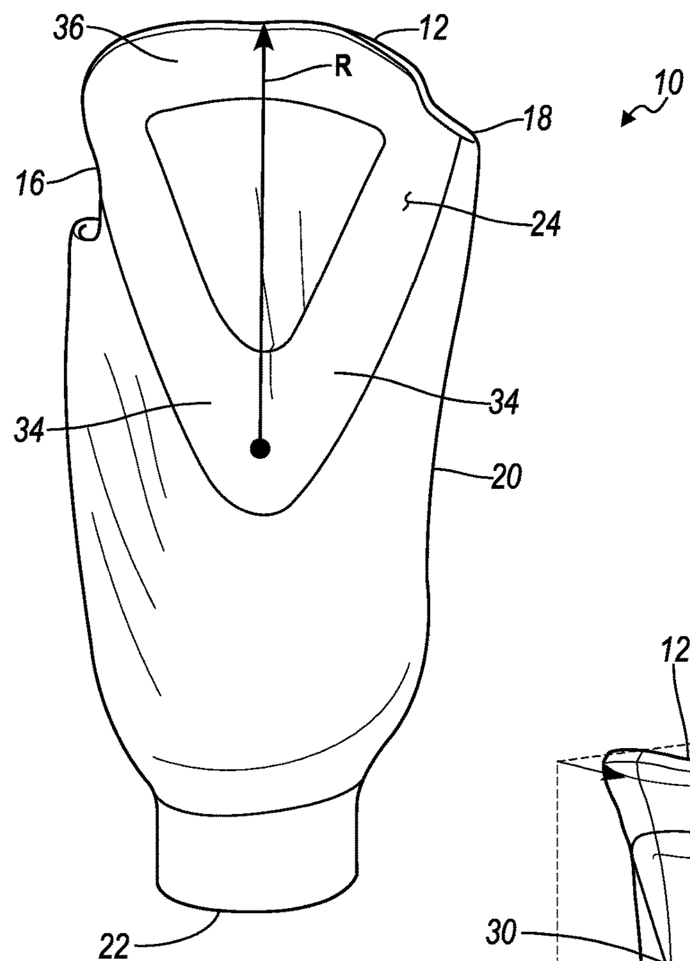
FIG. 1 is a lateral view of a prosthetic socket for use in a prosthetic limb according to the principles of the present invention.
Figure 2:
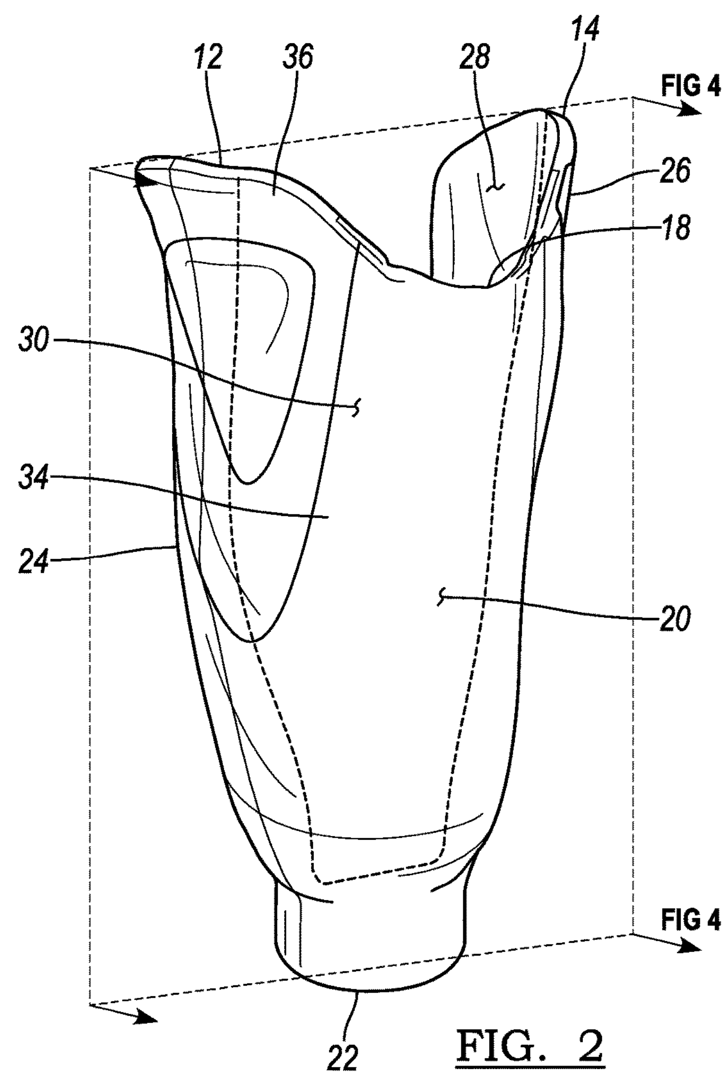
FIG. 2 is a perspective view of a prosthetic socket for use in a prosthetic limb according to the principles of the present invention.
Figure 3:
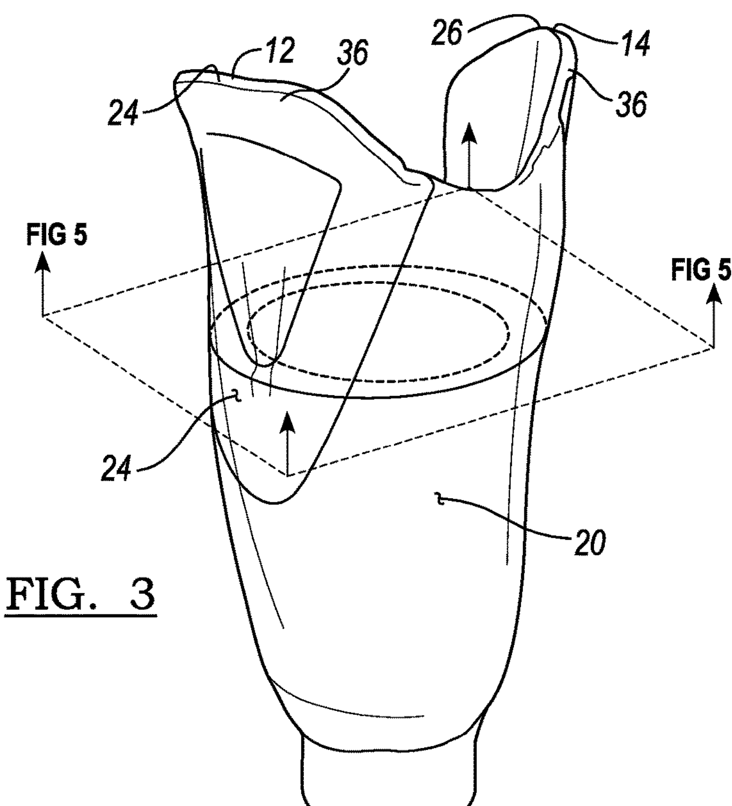
FIG. 3 is a perspective view of a prosthetic socket for use in a prosthetic limb according to the principles of the present invention.

Referring to FIGS. 1-3, a prosthetic socket of a prosthetic limb is illustrated and will now be described. Generally indicated by the reference number 10, the prosthetic socket 10 includes a medial fin 12, a lateral fin 14 (shown more clearly in FIG. 2), a posterior edge 16, an anterior edge 18, a socket body 20, a distal end 22, a medial structural member 24, a lateral structural member 26, an interior surface 28, and an exterior surface 30. More particularly, the medial fin 12, lateral fin 14, posterior edge 16, and anterior edge 18 combine to form a circumferential top edge 32 of the prosthetic socket. The height of the medial fin 12 and lateral fin 14 extends beyond the posterior and anterior edges 16, 18 which have a convex or scalloped shape. The medial 12 and lateral fins 14 have a top edge that generally follows a radius R curvature. The distal end 22 of the prosthetic socket 10 includes and attachment mechanism 25 for fixing a distal prosthetic component (not shown) to the prosthetic socket 10.

The shape of the interior surface 28 of the prosthetic socket 10 is generally a negative impression of a residual limb of a patient. Thus the interior surface 28 is tailored to the shape of the residual limb. There are several methods available to provide an interior surface 28 that is fitted to the particular patient's residual limb. One method in particular that is contemplated by this invention is to create a CAD model based on a scan of the residual limb. The scan is completed using a laser based scanning device, however, other types of devices made for taking measurements of objects have been considered by the present invention. Once the CAD model is generated from the scan of the residual limb, the interior surface 28 is created from the CAD model.

Regarding the design of the exterior surface 30 of the prosthetic socket 10, two major design considerations are weight and strength. As in most cases, when contemplating a particular material there is an inverse relationship between weight and strength. While the interior surface 28 of the prosthetic socket 10 is tailored to the shape of the residual limb, the shape of the exterior surface 30 is partially based on the shaped of the interior surface 28 and partially based on the forces applied to the prosthetic socket 10. In general, the forces that act on the prosthetic socket 10 are from two sources; the residual limb and the distal prosthetic component (not shown).

As stated above, the prosthetic socket 10 also includes a medial structural member 24, a lateral structural member 26. The structural members 24, 26 are defined by a raised portion of the outer surface 30 having a distinctive shape of a triangle 32 with two straight members 34 and an arch member 36. The arch member 36 of the medial structural member 24 is disposed on the prosthetic socket 10 such that the arch member 36 is co-located with the medial fin 12. Likewise, the arch member 36 of the lateral structural member 26 is disposed on the prosthetic socket 10 such that the arch member 36 is co-located with the lateral fin 14. The two straight members 34 of each of the structural members 24, 26 connect with the arch member 36 at the anterior and posterior ends 38, 40 of the arch members 36.

Figure 4:
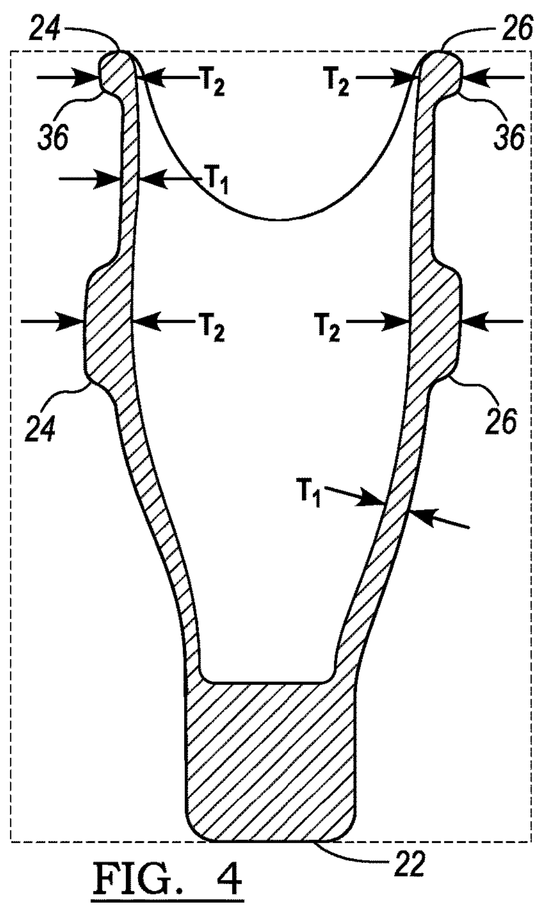
FIG. 4 is a front cross section of the prosthetic socket, as shown in FIG. 2, for use in a prosthetic limb according to the principles of the present invention.
Figure 5:
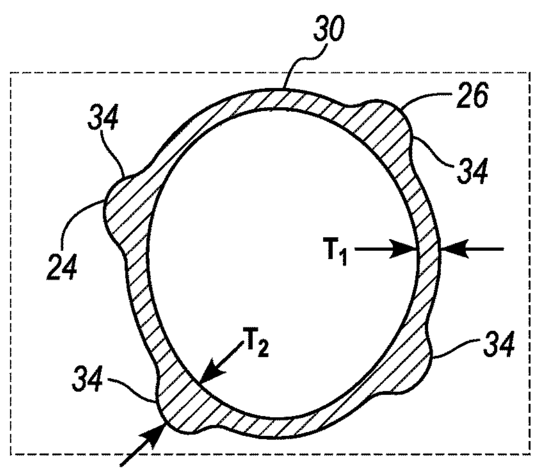
FIG. 5 is a top cross section of a prosthetic socket, as shown in FIG. 3, for use in a prosthetic limb according to the principles of the present invention.

Turning now to FIGS. 4 and 5, cross sections of the prosthetic socket 10 of FIGS. 2 and 3 are illustrated and will now be described. As stated above, the design of the exterior surface 30 of the prosthetic socket 10 is based on minimizing the weight of the prosthetic socket 10 while also meeting specific strength requirements. In order to minimize weight, the wall thickness $T_1$ between the interior surface 28 and exterior surface 30 in areas that do not include the medial and lateral structural members 24, 26 range from about 0.1 mm to about 20 mm. Alternatively, the wall thickness T2 of the structural members 24, 26 between the interior surface 28 and exterior surface 30 range from about 0.25 mm to about 100 mm.

Figure 6:
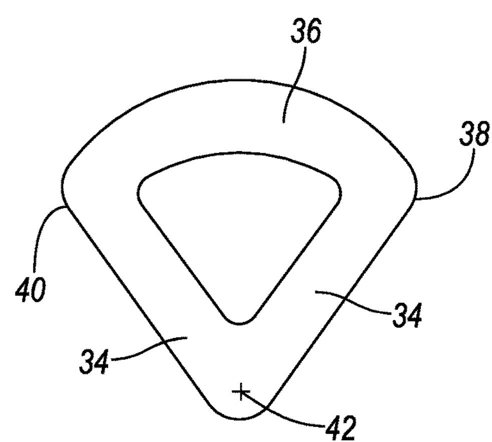
FIG. 6 is a front view of a structural member of a prosthetic socket according to the principles of the present invention.
Figure 7:
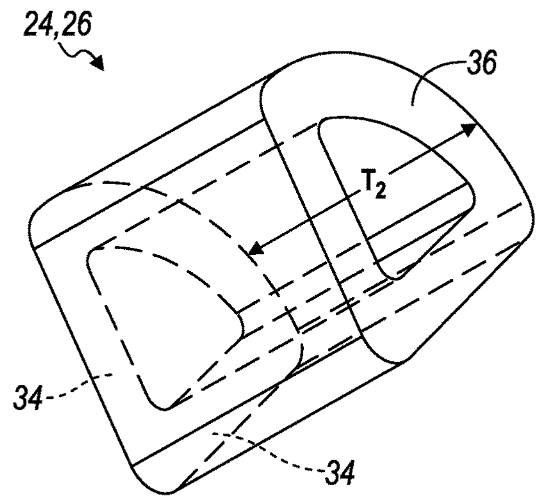
FIG. 7 is a perspective view of a structural member of a prosthetic socket according to the principles of the present invention.
Figure 8:
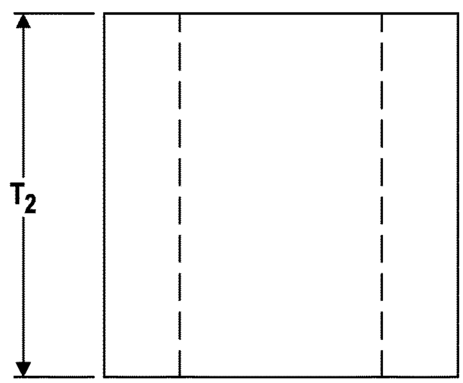
FIG. 8 is a top view of a structural member of a prosthetic socket according to the principles of the present invention.

Referring now to FIGS. 6-8, an example of the medial and lateral structural members 24, 26 are illustrated and will now be described. The structural members 24, 26 include a pair of straight members or sides 34 and an arch member 36. The arch member 36 includes a posterior end 38 and an anterior end 40. The pair of straight members 34 each include a distal end 42 and a proximal end 44. The distal ends 42 of the straight members 34 are fixedly connected. The proximal end 44 of one of the straight members 34 is fixedly connected to the posterior end 38 of the arch member and the proximal end of the other of the straight members 34 is fixedly connected to the anterior end 40 of the arch member 36. The depth or thickness $T_2$ of the structural member 24, 26 range from about 0.25 mm to about 100 mm. In one example of the present invention, the structural members 24, 26 are a continuous one-piece member. However, other examples may consider several separate members of the structural members 24, 26 without being outside the scope of the present invention.

Figure 9:
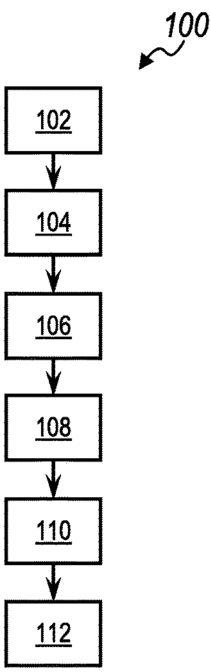
FIG. 9 is a flowchart containing the steps of a method of manufacturing a prosthetic socket according to the principles of the present invention.

Turning now to FIG. 9, a flowchart is shown illustrating the steps of a method 100 of manufacturing the prosthetic socket 10 previously described. The method includes a first step 102 of making a CAD model of the surface of a residual limb of a patient that is being fitted with a prosthetic limb. The CAD model can be created by using a surface scanning tool that uses a laser measuring device to convert the surface of the residual limb into digital surface data. A second step 104 converts the CAD model of the surface data into a volume model by adding wall thickness data. A third step 106 adds a scaled digital version of the medial structure member 24 and the lateral structured member 26 to the volume model through adding additional wall thickness in the portions of the volume model that represent the structural members 24, 26. A fourth step 108 checks the resulting volume model for voids or other inconsistencies. A fifth step 110 converts the volume model to a three dimensional printing path file. A sixth step 112 commands a three dimensional printer to print a prosthetic socket 10 using the three dimensional printing path file.

The description of the invention is merely exemplary in nature and variations that do not depart from the spirit of the invention are intended to be within the scope of the invention. Such variations are not to be regarded as a departure from the spirit and scope of the invention.

We claim:

1. A prosthetic socket for a prosthetic limb, the prosthetic socket comprising:

a socket body comprising a distal end and a top edge opposite the distal end, and wherein the distal end comprises a prosthetic component attachment mechanism, and a first structural member defined by a plurality of first portions raised from the outer surface of the socket body, the first raised portions having a triangular shape and comprising a first straight portion, a second straight portion, and a first arch portion, and wherein the first structural member is disposed on a medial, exterior surface of the socket body and wherein the socket body within the triangular shape of the first structural member exhibits a first wall thickness that is less than a second wall thickness of the first structural member; and wherein the first straight portion of the first structural member comprises a first end fixed to a second end of the second straight portion of the first structural member, a third end of the first arch portion is fixed to a fourth end of the first straight portion, and a fifth end of the first arch portion is fixed to a sixth end of the second straight portion of the first structural member.

2. The prosthetic socket of claim 1 wherein the socket body further comprises a medial fin disposed on the top edge of the socket body and the first arch portion of the first structural member is disposed on the medial fin of the top edge of the socket body.

3. The prosthetic socket of claim 2 wherein the socket body further comprises a second structural member having a third straight portion, a fourth straight portion, and a second arch portion, and wherein the second structural member is disposed on an lateral exterior surface of the socket body.

4. The prosthetic socket of claim 3 wherein the third straight portion of the second structural member comprises a seventh end fixed to an eighth end of the fourth straight portion of the second structural member, a ninth end of the second arch portion is fixed to a tenth end of the third straight portion, and an eleventh end of the second arch portion is fixed to a twelfth end of the fourth straight portion of the second structural member.

5. The prosthetic socket of claim 4 wherein the socket body further comprises a lateral fin disposed on the top edge of the socket body and the second arch portion of the second structural member is disposed on the lateral fin of the top edge of the socket body.

6. The prosthetic socket of claim 5 wherein the socket body further comprises a posterior edge and an anterior edge, the posterior edge is disposed on the top edge connecting the medial fin with the lateral fin, the anterior edge is disposed on the top edge opposite the posterior edge connecting the medial fin to the lateral fin, and the posterior edge and anterior edge have a scalloped shape.

7. The prosthetic socket of claim 6 wherein the socket body further comprises an interior surface having a negative shape of a residual limb of a wearer.

8. The prosthetic socket of claim 1 wherein the first wall thickness is from about 0.1 mm to about 20 mm.

9. The prosthetic socket of claim 8 wherein the second wall thickness is from about 0.25 mm to about 100 mm.

10. A prosthetic socket for a prosthetic limb, the prosthetic socket comprising:

a socket body comprising a distal end and a top edge opposite the distal end, and wherein the distal end comprises a prosthetic component attachment mechanism and the top edge comprises a medial fin, a lateral fin, a posterior edge and an anterior edge;

a first structural member defined by a plurality of first portions raised from the outer surface of the socket body, the first raised portions having a triangular shape and comprising a first straight portion, a second straight portion, and a first arch portion, and wherein the first structural member is disposed on a medial exterior surface of the socket body and wherein the socket body within the triangular shape of the first structural member exhibits a first wall thickness that is less than a second wall thickness of the first structural member; and a second structural member defined by a plurality of second portions raised from the outer surface of the socket body, the second raised portions having a triangular shape and including a third straight portion, a fourth straight portion, and a second arch portion, and wherein the second structural member is disposed on a lateral exterior surface of the socket body, wherein the first straight portion of the first structural member comprises a first end fixed to a second end of the second straight portion of the first structural member, a third end of the first arch portion is fixed to a fourth end of the first straight portion, and a fifth end of the first arch portion is fixed to a sixth end of the second straight portion of the first structural member.

11. The prosthetic socket of claim 10 wherein the first arch portion of the first structural member is disposed on the medial fin of the top edge of the socket body.

12. The prosthetic socket of claim 11 wherein the third straight portion of the second structural member comprises a seventh end fixed to an eighth end of the fourth straight portion of the second structural member, a ninth end of the second arch portion is fixed to a tenth end of the third straight portion, and an eleventh end of the first arch portion is fixed to a twelfth end of the fourth straight portion of the second structural member.

13. The prosthetic socket of claim 12 wherein the second arch portion of the second structural member is disposed on the lateral fin of the top edge of the socket body.

14. The prosthetic socket of claim 13 wherein a first cross section of the socket body includes a first wall thickness from about 0.1 mm to about 20 mm.

15. The prosthetic socket of claim 14 wherein a second cross section of the first structural member includes a second wall thickness from about 0.25 mm to about 100 mm.

16. The prosthetic socket of claim 15 wherein the posterior edge is disposed on the top edge connecting the medial fin with the lateral fin, the anterior edge is disposed on the top edge opposite the posterior edge connecting the medial fin to the lateral fin, and the posterior edge and anterior edge have a scalloped shape.

17. A method of manufacturing a prosthetic socket for a wearer, the method comprising:

creating a CAD model of surface data of a surface of a residual limb of the wearer;

converting the CAD model of surface data into a CAD model of volume data of a socket body by adding wall thickness to the CAD model of surface data;

adding a CAD model of volume data of a medial structural member and a lateral structural member to the CAD model of volume data of the socket body resulting in a CAD model of volume data of the prosthetic socket;

converting the CAD model of volume data of the prosthetic socket to a three dimensional print path file;

printing the three dimensional print path file using a three dimensional printer; and adding a CAD model of volume data of a distal end to the CAD model of volume data of the prosthetic socket, wherein the medial structural member includes a plurality of first portions raised from the outer surface of the socket body, the first raised portions having a triangular shape and including a first straight portion, a second straight portion, and a first arch portion, and wherein the medial structural member is disposed on a medial, exterior surface of the socket body, and wherein the socket body within the triangular shape of the medial structural member exhibits a first wall thickness that is less than a second wall thickness of the medial structural member and wherein the lateral structural member includes a second plurality of second portions raised from the outer surface of the socket body, the second raised portions having a triangular shape and including a third straight portion, a fourth straight portion, and a second arch portion, and wherein the second structural member is disposed on a lateral exterior surface of the socket body.

* * * * *